United States Patent [19]
Harris

[11] Patent Number: 5,898,086
[45] Date of Patent: Apr. 27, 1999

[54] PROCESS FOR MAKING ALKYL ETHER GLYCEROLS

[75] Inventor: Eugene G. Harris, West Chester, Ohio

[73] Assignee: Henkel Corporation, Gulph Mills, Pa.

[21] Appl. No.: 08/820,520

[22] Filed: Mar. 19, 1997

Related U.S. Application Data

[60] Provisional application No. 60/015,883, Apr. 19, 1996.

[51] Int. Cl.$^6$ .............................. C07C 41/00; C07C 43/00
[52] U.S. Cl. .......................... 568/579; 568/671; 568/675
[58] Field of Search .................................... 568/579, 671, 568/675

[56] References Cited

U.S. PATENT DOCUMENTS

| | | | |
|---|---|---|---|
| 3,850,831 | 11/1974 | Hellsten et al. | 252/99 |
| 3,976,588 | 8/1976 | McLaughlin | 252/117 |
| 5,137,660 | 8/1992 | Mazur et al. | 536/18.2 |

FOREIGN PATENT DOCUMENTS

| | | |
|---|---|---|
| 0649829 | 4/1995 | European Pat. Off. . |
| 62-198632 | 9/1987 | Japan . |
| 09012491 | 1/1997 | Japan . |

*Primary Examiner*—Marian C. Knode
*Assistant Examiner*—Everett White
*Attorney, Agent, or Firm*—Ernest G. Szoke; Wayne C. Jaeschke; Steven J. Trzaska

[57] ABSTRACT

A process for making alkyl ether glycerols involving: (a) providing a feedstock component having at least one terminal hydroxyl group selected from the group consisting of glycerides and polyols; (b) providing a heavy metal catalyst; and (c) contacting the feedstock component with the heavy metal catalyst.

10 Claims, No Drawings

PROCESS FOR MAKING ALKYL ETHER GLYCEROLS

BENEFIT OF EARLIER FILING DATE UNDER 37 CFR 1.78(A)(4)

This application claims the benefit of earlier filed and copending provisional application Ser. No. 60/015,883 filed on Apr. 19, 1996.

FIELD OF THE INVENTION

The present invention generally relates to a process for making alkyl ether glycerols. More particularly, there is provided a process for producing alkyl ether glycerols by reducing glycerides using a heavy metal catalyst.

BACKGROUND OF THE INVENTION

It is known that various surfactants have been found to be useful in cleaning compositions, such as shower gels, shampoos, and light duty detergents such as dishwashing detergents. In these types of compositions, good foamability is a prerequisite. The most widely used surfactants in these types of compositions are anionic surfactants such as alkyl sulfates, alkyl ether sulfates, sulfonates, sulfosuccinates and sarcosinates.

It is sometimes advantageous to use mixtures of surfactants in cleaning compositions when the surfactants can serve different functions, e.g., one serving to improve foamability and another serving to adjust viscosity. Regardless of the specific types of surfactants which are employed in a composition, the fact remains that the use of surfactants is very prevalent in our society.

An object of the present invention is to provide a process for effectively producing intermediates used in making surfactants.

SUMMARY OF THE INVENTION

The present invention is thus directed to a process for making alkyl ether polyols involving:

(a) providing a feedstock selected from the group consisting of glycerides and polyols;

(b) providing a heavy metal catalyst; and (c) contacting the feedstock with the heavy metal catalyst.

DESCRIPTION OF THE INVENTION

Unless otherwise indicated, all numbers expressing quantities of ingredients or reaction conditions are understood as being modified in all instances by the term "about".

The feedstock which may be used in the process of the present invention is generally characterized by the presence of at least one terminal hydroxyl group capable of being etherified. Examples of suitable feedstock components include, but are not limited to, mono-, di-, and triglycerides derived from fats and oils which may be saturated or unsaturated, linear or branched and having from 8 to 22 carbon atoms, as well as polyols such as glycerol, and the like. In a particularly preferred embodiment of the present invention, the feedstock employed is a monoglyceride.

The heavy metal catalyst is employed in the present invention in order to etherify the feedstock component. For example, if a glyceride derived from a fat or oil is employed as the feedstock component, the catalyst reduces the ester linkage thereof, thereby forming the desired alkyl ether glycerol component. Examples of suitable heavy metal catalysts which may be employed in accordance with the present invention include, but are not limited to, copper/zinc catalysts and copper/chromite catalysts.

In a particularly preferred embodiment of the present invention, the heavy metal catalyst used is a copper/zinc catalyst. According to one example of how to produce the copper/zinc catalysts, the alkali metal compound is added in portions to the aqueous solution containing the copper(II) and zinc(II) salts at 50 to 90° C. until a pH value of at least 6 is reached. A pH in the range from 8 to 9 has proven to be optimal for precipitation.

The resulting mixture of basic copper(II) and zinc(II) carbonate is separated from the aqueous solution, for example by filtration or centrifugation, washed and dried.

The aqueous solutions may contain the water-soluble copper(II) and zinc(II) salts in molar ratios of 1:10 to 10:1. Particularly active catalysts are obtained when molar ratios of 1:2 to 2:1 and, more particularly, 1:1 are selected.

In the context of the invention, water-soluble copper(II) and zinc(II) salts are understood to be the sulfates, nitrates and halides free from or containing water of crystallization. Copper(II) nitrate and zinc(II) nitrate are preferably used because the anion is particularly easy to wash out after precipitation of the hydroxides.

After precipitation, the dried catalyst is calcined for 1 to 60 minutes and preferably for 5 to 15 minutes at a temperature in the range from 400 to 600° C. and preferably at a temperature in the range from 450 to 550° C. In this calcination step, the basic copper/zinc carbonates are converted into irregular crystallite fragments which may then be lightly compacted.

For use in a fixed bed, the catalyst has to be converted into particulate form. To this end, the catalyst may be converted into cylindrical pellets, for example by means of a rotary pelleting machine, or into cylindrical extrudates in a screw extruder preceded by a breaker plate.

Preferably, graphite is added at the pelletizing stage to facilitate the making of the pellets by providing lubrication and to assist in binding the catalyst together. The amount of graphite that can be added is from about 1% to about 10% by weight. Preferably, the amount of graphite will be from 2 to 7%.

In this form, the copper/zinc catalysts according to the invention are suitable for the direct hydrogenation of fatty acid lower alkyl esters and deacidified fatty acid glyceride esters. Before they are used in the hydrogenation process, the catalysts normally have to be activated with hydrogen or with a hydrogen-containing gas mixture.

The process of the present invention enables the reduction reaction of the feedstock component to be carried out under surprisingly low temperature and hydrogen pressures and increased feed rates. According to one embodiment of the present invention, the feedstock component, preferably a monoglyceride, is contacted with the heavy metal catalyst, preferably a copper/zinc catalyst as described above, under the following reaction conditions: (i) a temperature ranging from about 150 to about 260° C.; (ii) hydrogen pressure ranging from about 2000 to about 4500 psi; (iii) a feed rate ranging from about 5000 to about 15000 scfm (standard cubic feet per minute);

and (iv) with the amount of feedstock component being reacted ranging from about 20 to about 40 gpm (grams per minute).

What is claimed is:

1. A process for making alkyl ether glycerols comprising:
   (a) providing a feedstock component having at least one terminal hydroxyl group selected from the group consisting of glycerides and polyols;
   (b) providing a heavy metal catalyst; and
   (c) contacting the feedstock component with the heavy metal catalyst.

2. The process of claim 1 wherein the feedstock component is a monoglyceride.

3. The process of claim 1 wherein the heavy metal catalyst is a copper/zinc catalyst.

4. The process of claim 1 wherein the heavy metal catalyst is a copper/chromide catalyst.

5. The process of claim 1 wherein the feedstock component is contacted with the heavy metal catalyst at a temperature ranging from about 150 to about 260° C.

6. The process of claim 1 wherein the feedstock component is contacted with the heavy metal catalyst at a hydrogen pressure ranging from about 2,000 to about 4,500 psi.

7. The process of claim 1 wherein the feedstock component is contacted with the heavy metal catalyst at a feed rate ranging from about 5,000 to about 15,000 scfm.

8. The process of claim 1 wherein from about 20 to about 40 gpm of the feedstock component is contacted with the heavy metal catalyst.

9. A process for making alkyl ether glycerols comprising:
   (a) providing a monoglyceride feedstock;
   (b) providing a copper/zinc catalyst; and
   (c) contacting the monoglyceride feedstock with the copper/zinc catalyst at a temperature of from about 150 to about 260° C., a hydrogen pressure of from about 2,000 to about 4,500 psi, and a feed rate of from about 5,000 to about 15,000 scfm.

10. The process of claim 9 wherein from about 20 to about 40 grams per minute of the monoglyceride feedstock is contacted with the copper/zinc catalyst.

* * * * *